(12) United States Patent
Onishi et al.

(10) Patent No.: US 8,176,771 B2
(45) Date of Patent: May 15, 2012

(54) ENDOSCOPE WASHING AND DISINFECTING APPARATUS AND LEAK DETECTION METHOD PERFORMED BY THE APPARATUS

(75) Inventors: Hideto Onishi, Hachioji (JP); Kenichi Kobayashi, Hachioji (JP); Keisuke Nozaki, Zama (JP); Shintaro Suzuki, Hachioji (JP); Naoya Taya, Hachioji (JP); Masahiko Tomita, Hachioji (JP); Toshiaki Noguchi, Tachikawa (JP); Eiri Suzuki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 568 days.

(21) Appl. No.: 12/266,890

(22) Filed: Nov. 7, 2008

(65) Prior Publication Data

US 2009/0158539 A1  Jun. 25, 2009

(30) Foreign Application Priority Data

Dec. 21, 2007  (JP) .................................. 2007-330793

(51) Int. Cl.
   *G01M 3/06*   (2006.01)
   *A61L 2/18*   (2006.01)
(52) U.S. Cl. .................... 73/45.5; 73/40; 422/6; 422/28; 600/118
(58) Field of Classification Search ............. 73/40, 45.5; 422/6, 14, 28, 31; 600/118
   See application file for complete search history.

(56) References Cited

U.S. PATENT DOCUMENTS

| | | | | |
|---|---|---|---|---|
| 4,506,544 A | * | 3/1985 | Shimizu | ......................... 73/45.5 |
| 5,303,576 A | * | 4/1994 | Erdelsky | ......................... 73/40 |
| 5,494,530 A | * | 2/1996 | Graf | ............................... 134/18 |
| 5,882,589 A | * | 3/1999 | Mariotti | ......................... 422/28 |
| 6,068,815 A | * | 5/2000 | Oberleitner et al. | ............ 422/28 |
| 6,408,682 B2 | * | 6/2002 | Greszler | ........................... 73/40 |
| 6,412,334 B1 | | 7/2002 | Kral et al. | |
| 6,482,358 B1 | * | 11/2002 | Kelsch et al. | .................... 422/28 |
| 6,656,438 B1 | * | 12/2003 | Kinoshita et al. | ............. 422/292 |
| 6,899,674 B2 | * | 5/2005 | Viebach et al. | ................ 600/152 |
| 7,875,126 B2 | * | 1/2011 | Noguchi et al. | ................ 134/42 |
| 7,901,349 B2 | * | 3/2011 | Feld et al. | ...................... 600/155 |
| 7,905,831 B2 | * | 3/2011 | Noguchi et al. | .............. 600/132 |
| 2001/0032494 A1 | * | 10/2001 | Greszler | ........................... 73/40 |
| 2002/0064479 A1 | * | 5/2002 | Nakanishi et al. | ............. 422/28 |
| 2003/0181785 A1 | * | 9/2003 | Viebach et al. | ................ 600/152 |
| 2004/0054258 A1 | * | 3/2004 | Maeda et al. | ................. 600/152 |
| 2004/0118413 A1 | * | 6/2004 | Williams et al. | .............. 128/898 |

(Continued)

FOREIGN PATENT DOCUMENTS

EP   1 757 313 A1   2/2007

(Continued)

*Primary Examiner* — David Rogers
(74) *Attorney, Agent, or Firm* — Scully, Scott, Murphy & Presser, P.C.

(57) ABSTRACT

An endoscope washing and disinfecting apparatus includes: a connecting portion connected to a bending transmitting portion of an endoscope to transmit driving force; a distal end driving portion for transmitting the driving force to the bending transmitting portion through the connecting portion; a fluid supplying unit for supplying gas into an inner space of the endoscope; and a control unit for controlling a pressure detecting portion for detecting pressure in the inner space and the distal end driving portion to provide the bending portion with bending motion, and for determining occurrence or non-occurrence of water leak in the endoscope by comparing the pressure detected by the pressure detecting portion and a preset threshold.

7 Claims, 10 Drawing Sheets

U.S. PATENT DOCUMENTS

| | | | |
|---|---|---|---|
| 2005/0079094 A1* | 4/2005 | Mariotti et al. | 422/3 |
| 2005/0148819 A1* | 7/2005 | Noguchi et al. | 600/133 |
| 2005/0209507 A1* | 9/2005 | Suzuki et al. | 600/133 |
| 2006/0045798 A1* | 3/2006 | Wu et al. | 422/28 |
| 2006/0252991 A1 | 11/2006 | Kubach | |
| 2007/0060791 A1* | 3/2007 | Kubach | 600/117 |
| 2007/0169799 A1* | 7/2007 | Noguchi et al. | 134/56 R |
| 2007/0193605 A1* | 8/2007 | Kuroshima et al. | 134/18 |
| 2007/0238923 A1* | 10/2007 | Kubach | 600/118 |
| 2007/0251039 A1* | 11/2007 | Kobayashi et al. | 15/104.095 |
| 2008/0281158 A1* | 11/2008 | Miyagi et al. | 600/152 |
| 2008/0283095 A1* | 11/2008 | Suzuki et al. | 134/18 |
| 2009/0020142 A1* | 1/2009 | Miyako | 134/22.14 |
| 2009/0044845 A1* | 2/2009 | Cui et al. | 134/56 R |
| 2009/0192354 A1* | 7/2009 | Hasegawa | 600/118 |
| 2010/0189598 A1* | 7/2010 | Fraundorfer | 422/28 |

FOREIGN PATENT DOCUMENTS

| | | |
|---|---|---|
| EP | 1 785 150 A1 | 5/2007 |
| EP | 1 815 782 A2 | 8/2007 |
| JP | 05-168592 | 7/1993 |
| JP | 3109201 | 3/2005 |

* cited by examiner

ENDOSCOPE WASHING AND DISINFECTING APPARATUS AND LEAK DETECTION METHOD PERFORMED BY THE APPARATUS

This application claims the benefit of Japanese Application No. 2007-330793 filed in Japan on Dec. 21, 2007, the contents of which are incorporated herein by this reference.

BACKGROUND OF THE INVENTION

1. Field of the Invention

The present invention relates to an endoscope washing and disinfecting apparatus which detects water leak when the apparatus washes and disinfects an endoscope, and to a leak detection method performed by the apparatus.

2. Description of the Related Art

Endoscopes used for the purpose of examining or treating body cavities need to be washed and disinfected after being used. When an endoscope is used, garbage is attached not only to an outer surface of an insertion portion to be inserted into a body cavity, but also to the interiors of individual tubes, such as an air/water supply tube, a suction tube, a forward water supply tube and a treatment tool inserting tube. Therefore, after being used, the interiors of the individual tubes of an endoscope need to be washed and disinfected without fail, in addition to the outer surface of the endoscope.

When washing processes and disinfecting processes for an endoscope are carried out using an endoscope washing and disinfecting apparatus (hereinafter also referred to as a "washing apparatus"), the endoscope that has been used is placed, first, in a washing and disinfecting sink of a washing apparatus (hereinafter also referred to as a "washing sink"). Then, in order to wash and disinfect the interiors of the tubes of the endoscope, a plurality of supply nozzles of the washing apparatus for supplying fluid into the tubes are connected to a plurality of tube bases which are open in the outer surface of the endoscope. Also, an inner space base communicating with an inner space of the endoscope is connected to a leak detection nozzle for supplying gas. The leak detection nozzle is provided at the washing apparatus, in order to check whether or not holes or the like are formed which permit communication between the inner space of the endoscope and the outside, or, in order to perform leak detection for fining leaking points.

After the washing sink is closed with a cover member and processes are started, a predetermined amount of gas is supplied into the inner space of the endoscope through the leak detection nozzle and the inner space base. Then, pressure in the inner space is measured by a sensor, for example, and thereby leak detection is carried out.

If the leak detection results in "No leak occurred", washing processes are performed, which are followed by disinfecting processes. In the washing processes, washing solution is supplied into the washing sink until the amount of the washing solution reaches a predetermined level. Then, washing is started to wash the outer surface of the endoscope with the circulation of the washing solution. The washing solution in the washing sink, which has been sucked by a circulation pump, is discharged from the supply nozzles for introduction into the tubes through the tube bases and for washing of the interiors of the tubes.

After the washing processes have been completed, the washing solution on the outer surface of the endoscope and in the tubes is washed away with filtered tap water. The procedure then proceeds to the disinfecting processes, in which disinfectant solution that has been adjusted to have a predetermined concentration is supplied to the washing sink. Then, the disinfectant solution in the washing sink, which has been sucked by the circulation pump, is discharged from the supply nozzles for introduction into the tubes through the tube bases.

After the disinfectant solution has been supplied onto the outer surface of the endoscope and into the tubes, the endoscope is immersed in the disinfectant solution to be disinfected for a while. After the disinfecting processes have been completed, the disinfectant solution is washed away with filtered tap water. Then, air or alcohol is supplied onto the outer surface of the endoscope and into the tubes in order to facilitate drying, whereby a series of processes of the washing apparatus is ended.

Japanese Utility Model Registration No. 3109201 discloses a leak detection apparatus for endoscopes, in which an endoscope is immersed in water stored in a washing sink, and air is supplied into an inner space of the endoscope from an air pump to check damages caused on the endoscope. The leak detection apparatus mentioned above has a pressure sensor. The pressure sensor is provided at a discharge-side tube of a regulating valve which is provided at an air supply tube for supplying air. In the apparatus, a circuit is configured in such a way that a control unit, which has been inputted with alarm signals, outputs a stop instructing signal for an air pump and an alarming instructing signal for a buzzer. Thus, in the case where the regulating valve breaks down during leak detection to permit the pressure in an inner space of the endoscope to exceed a specified value, driving of the air pump is stopped to prevent the endoscope from being broken.

Also, Japanese Patent Application Laid-Open Publication No. 5-168592 discloses a washing apparatus having a leak detection function, in which air is supplied into an inner space of an endoscope while pressure variation is measured, so that air leak from the inner space can be detected, for the detection of water leak of the inner space. The apparatus is provided with a pressure-keeping portion which supplies air to the inner space of the endoscope during washing and disinfecting operation to keep the space in the state of being pressurized. Thus, water can be prevented from leaking into the inner space of the endoscope during the washing and disinfecting operation.

SUMMARY OF THE INVENTION

An endoscope washing and disinfecting apparatus of the present invention includes: a connecting portion for transmitting driving force, the connecting portion being connected to a bending transmitting portion of an endoscope comprising a distal end portion, a bending portion, an insertion portion, a grasping portion, and the bending transmitting portion provided at the grasping portion to provide the bending portion with bending motion; a distal end driving portion for transmitting driving force to the bending transmitting portion through the connecting portion; a fluid supplying unit for supplying gas into an inner space of the endoscope; a pressure detecting portion for detecting pressure in the inner space; and a control unit for controlling the distal end driving portion to provide the bending portion with bending motion, and for determining occurrence or nonoccurrence of water leak the endoscope by comparing the pressure detected by the pressure detecting portion with a preset threshold.

A leak detection method performed by an endoscope washing and disinfecting apparatus of the present invention includes: a connecting step for connecting an inner space base of an endoscope comprising a distal end portion, a bending portion, an insertion portion, a grasping portion, a bending transmitting portion provided at the grasping portion to provide the bending portion with bending motion, and the inner space base provided at the grasping portion and communicating with an inner space of the insertion portion, to a fluid supplying unit of the endoscope washing and disinfecting apparatus comprising a distal end driving portion for transmitting driving force to the bending transmitting portion through a connecting portion, the fluid supplying unit, and a pressure detecting portion; a pressurizing step for supplying gas to the inner space from the fluid supplying unit; a bending portion driving step for bending the bending portion by driving the distal end driving portion; a detecting step for detecting pressure in the inner space by the pressure detecting portion; and a determining step for determining occurrence or nonoccurrence of water leak in the endoscope by comparing the pressure in the inner space and a preset threshold.

DETAILED DESCRIPTION OF THE PREFERRED EMBODIMENTS

With reference to the drawings, hereinafter will be described an embodiment of the present invention.

Figure 1:
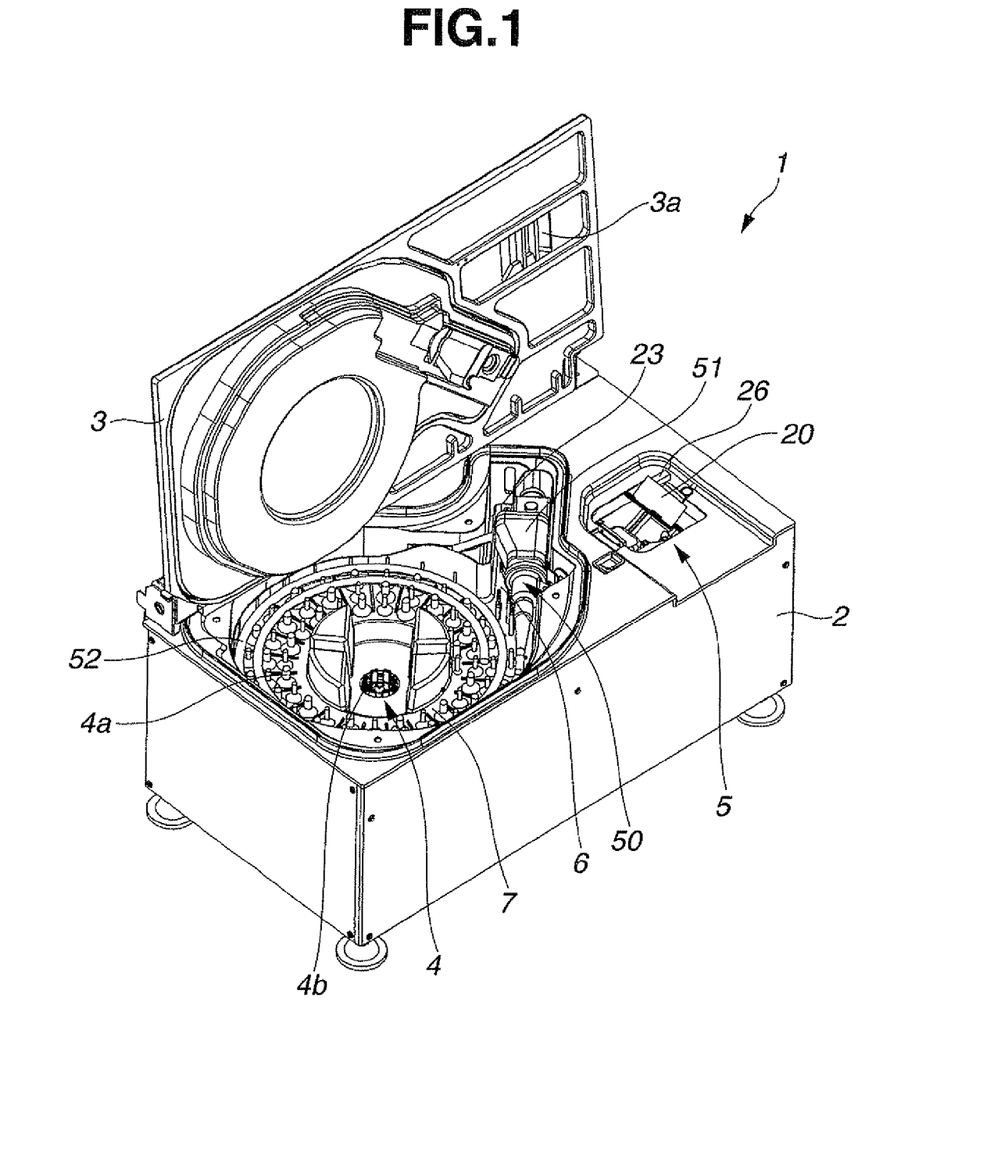
FIG. 1 is a perspective view illustrating an appearance of an endoscope washing and disinfecting apparatus in a state where a top cover is open, according to an embodiment of the present invention.
Figure 2:
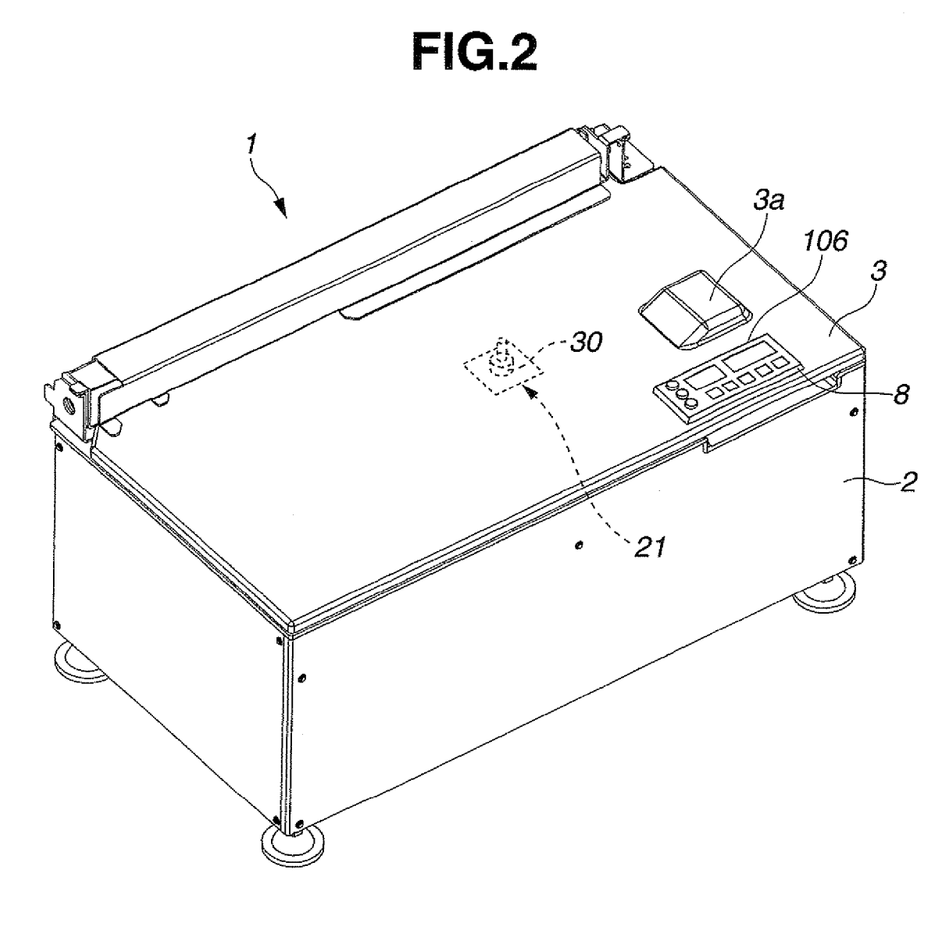
FIG. 2 is a perspective view illustrating an appearance of the endoscope washing and disinfecting apparatus in a state where the top cover is closed, according to the embodiment.
Figure 3:
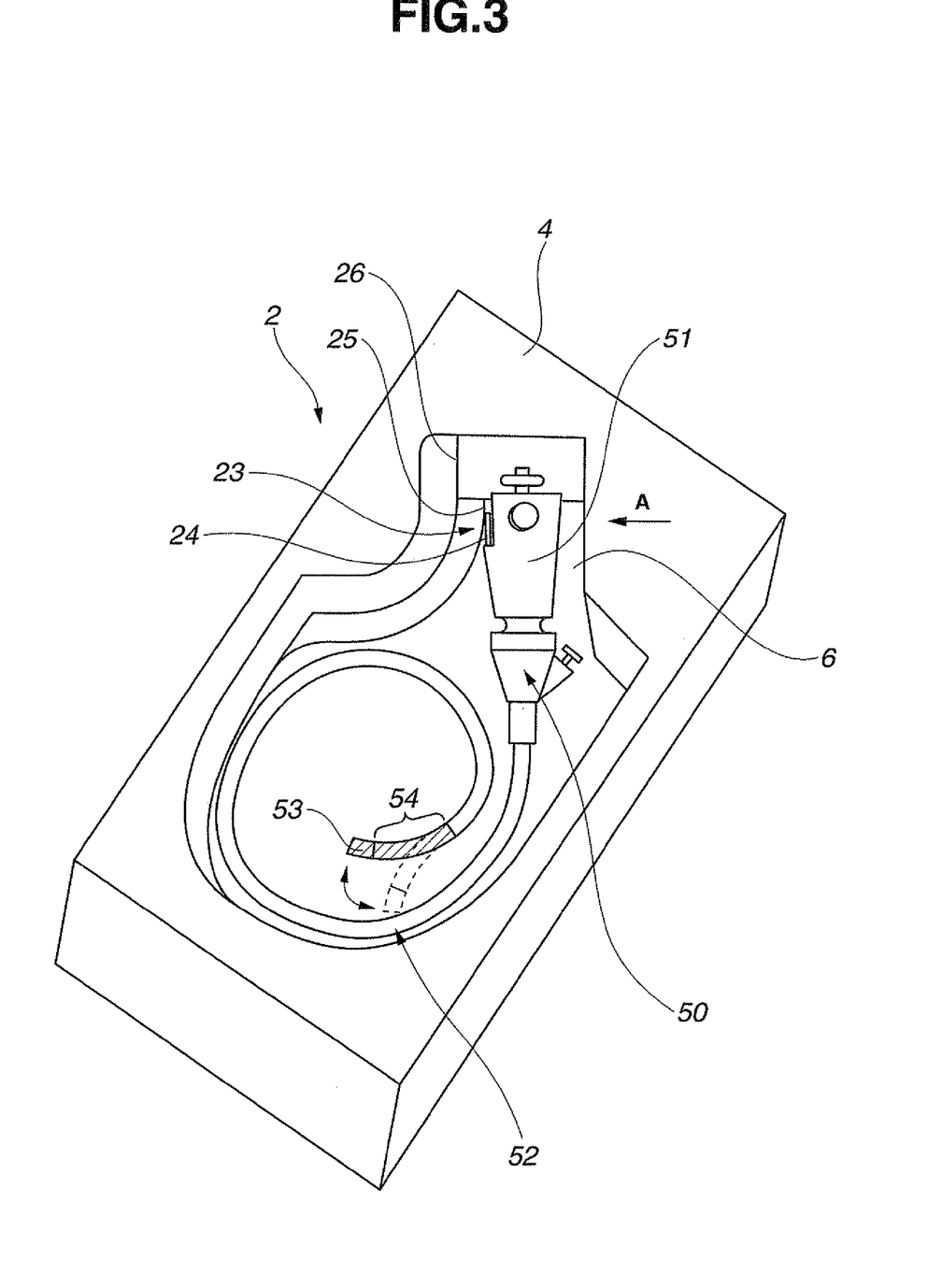
FIG. 3 is a perspective view illustrating a state where an endoscope is placed in a washing sink of the washing and disinfecting apparatus, with a grasping portion of the endoscope being connected to a connecting portion provided at the washing sink, according to the embodiment.
Figure 4:
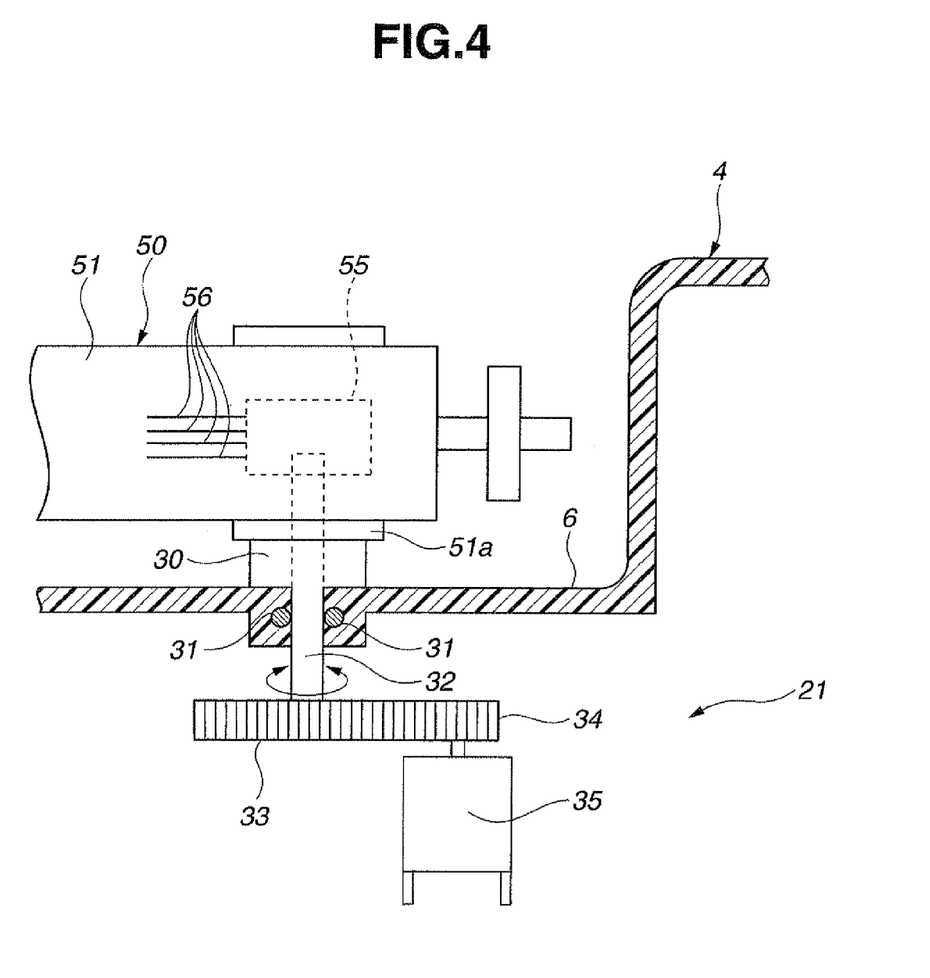
FIG. 4 is a cross-sectional view illustrating a configuration of each of a distal end driving portion, the connecting portion and the grasping portion of the endoscope to be connected to the connecting portion, in an apparatus body as viewed from a direction of an arrow "A" of FIG. 3.
Figure 5:
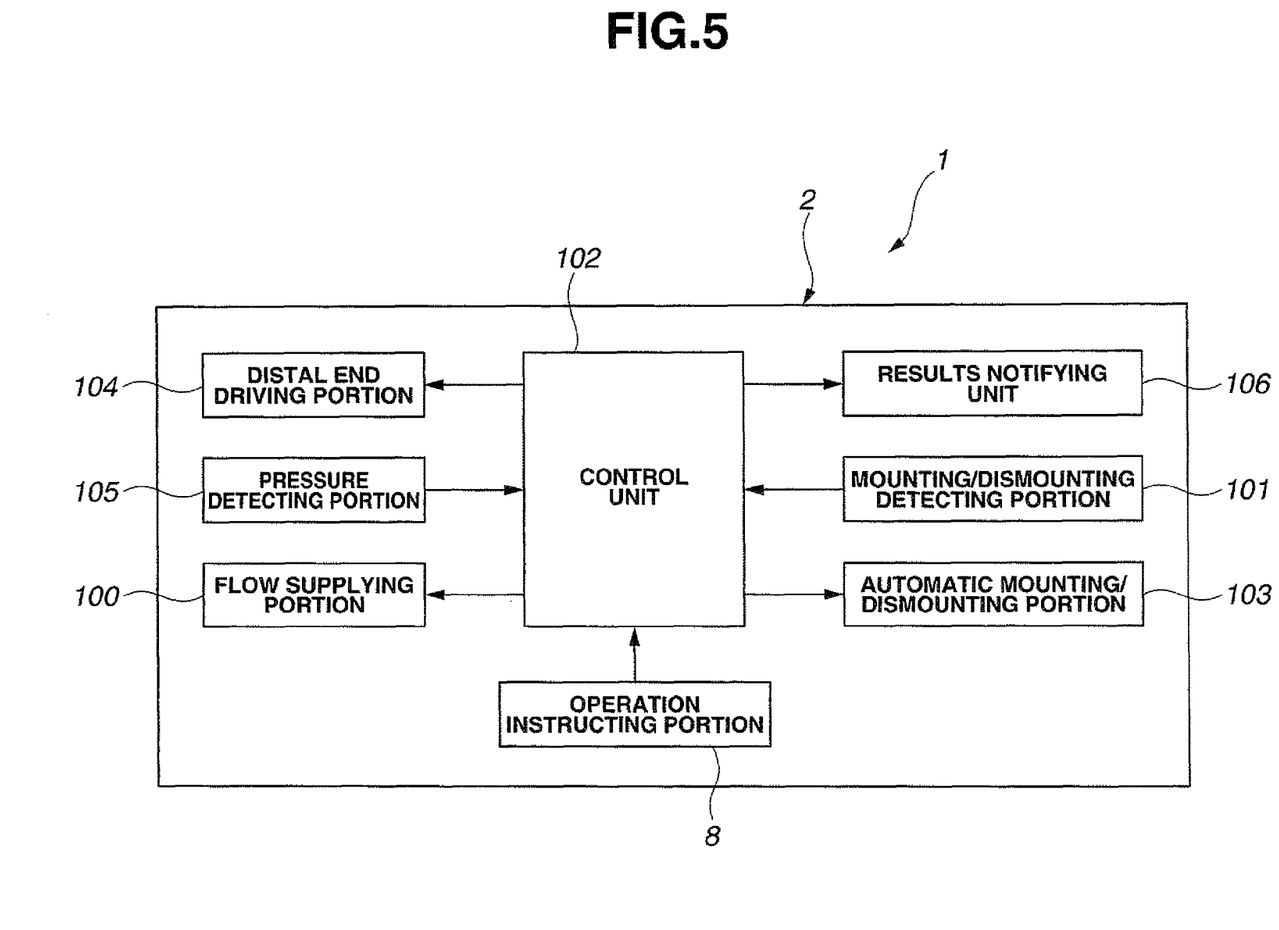
FIG. 5 is a block diagram illustrating a configuration of the endoscope washing and disinfecting apparatus, according to the embodiment.
Figure 6A:
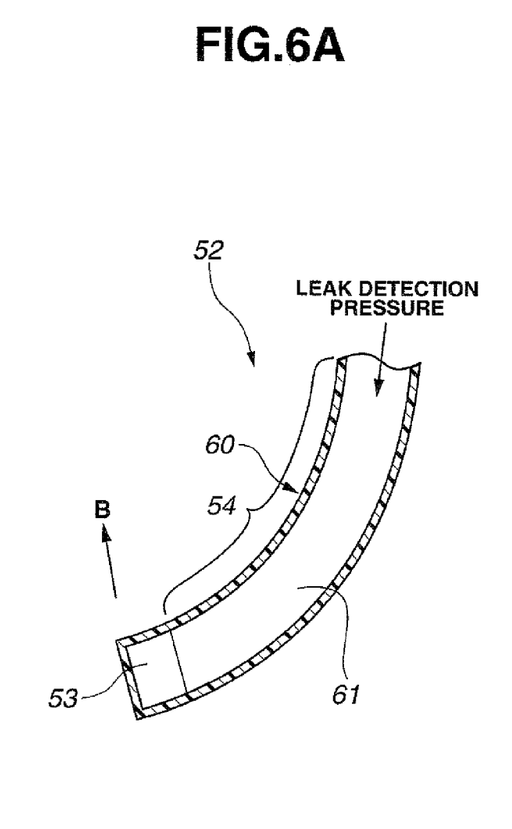
FIGS. 6A and 6B are explanatory views each illustrating motion of a bending portion when a leak detection method according to the embodiment is performed.
Figure 6B:
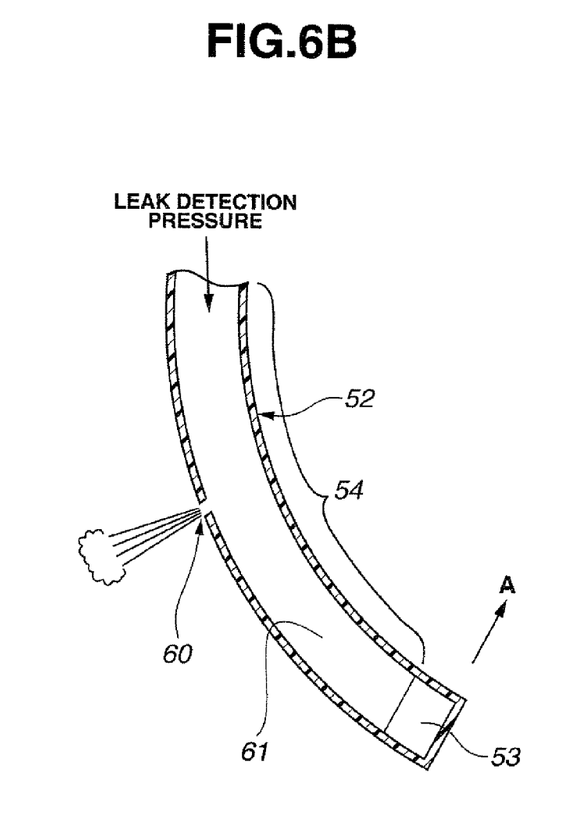
Figure 7:
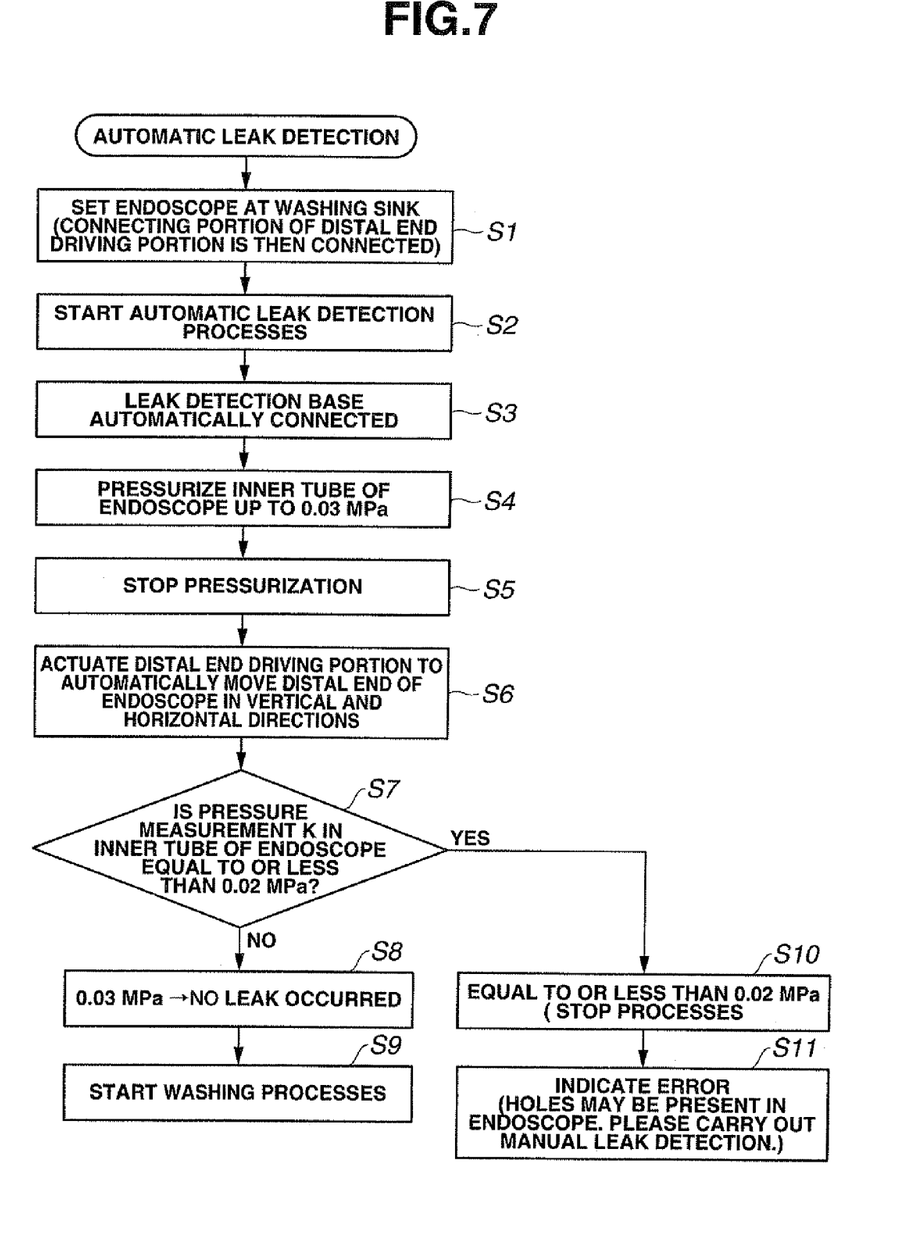
FIG. 7 is a flow diagram illustrating a control procedure of an automatic leak detection method performed by the endoscope washing and disinfecting apparatus, according to the present embodiment.
Figure 8:
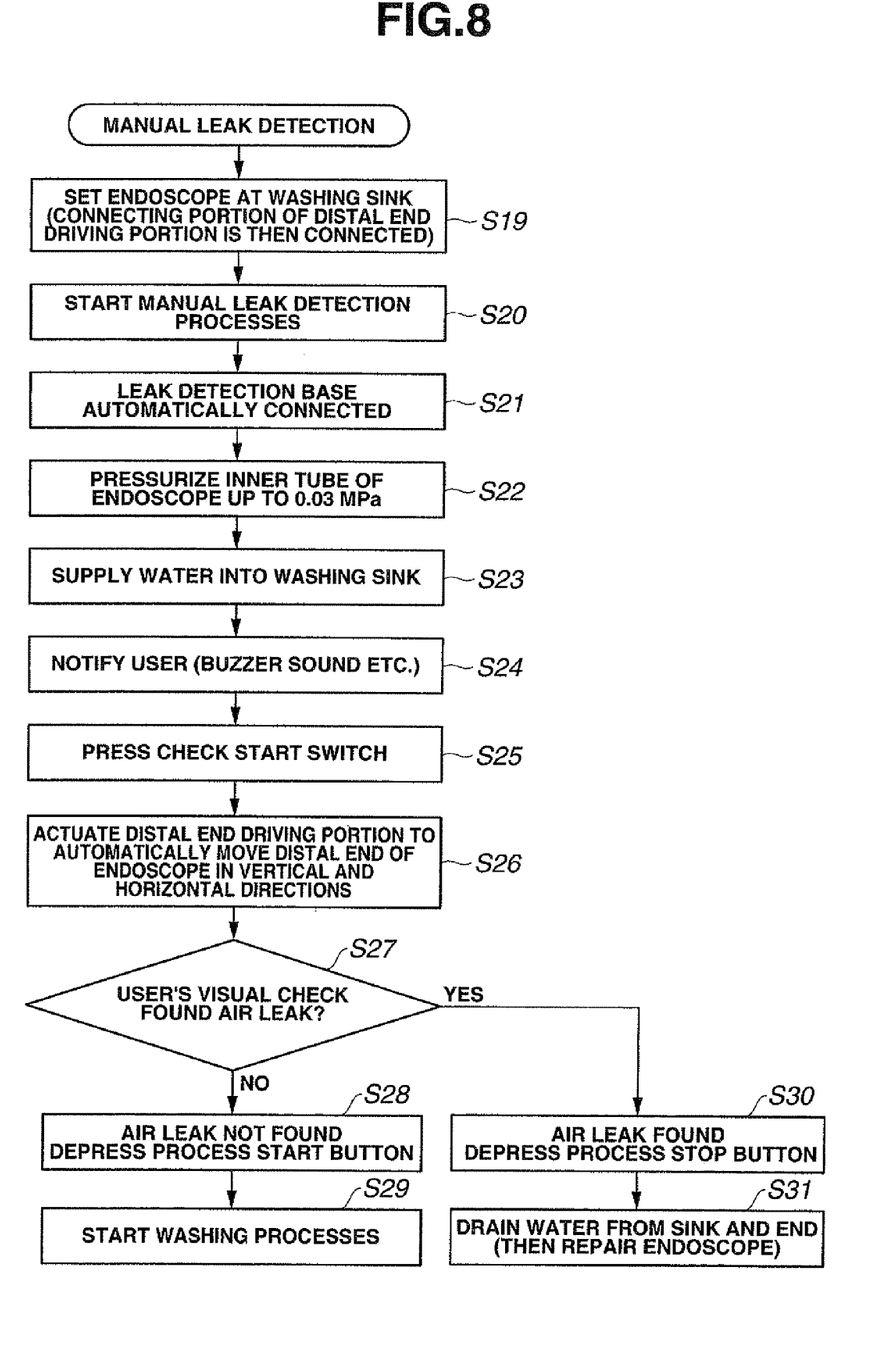
FIG. 8 is a flow diagram illustrating a control procedure of a manual leak detection method performed by the endoscope washing and disinfecting apparatus, according to the present embodiment.

FIGS. 1 to 8 illustrate an embodiment of the present invention. FIG. 1 is a perspective view illustrating an appearance of washing apparatus in a state where a top cover is open, according to the embodiment. FIG. 2 is a perspective view illustrating an appearance of the washing apparatus in a state where the top cover is closed, according to the embodiment. FIG. 3 is a perspective view illustrating a state where an endoscope is placed in a washing sink of the washing apparatus, with a grasping portion of the endoscope being connected to a connecting portion of the washing apparatus, according to the embodiment. FIG. 4 is a cross-sectional view illustrating a configuration of each of a distal end driving portion, the connecting portion and the grasping portion of the endoscope to be connected to the connecting portion, in an apparatus body as viewed from a direction of an arrow "A" of FIG. 3. FIG. 5 is a block diagram illustrating a configuration of the washing apparatus, according to the embodiment. FIGS. 6A and 6B are explanatory views each illustrating motion of a bending portion when a leak detection method according to the embodiment is performed. In particular, FIG. 6A illustrates a state where the bending portion is bent toward the side of a hole and FIG. 6B illustrates a state where the bending portion is bent toward the side opposite to the hole. FIGS. 7 and 8 each explain leak detection operation of the washing apparatus according to the embodiment. In particular, FIG. 7 is a flow diagram illustrating a control procedure of an automatic leak detection method and FIG. 8 is a flow diagram illustrating a control procedure of a manual leak detection method.

As shown in FIG. 1, a washing apparatus 1 according to the present embodiment mainly includes an apparatus body 2 and a top cover 3 serving as a lid, which is provided at a top face of the apparatus body 2 and can be freely opened/closed.

The apparatus body 2 has a top face portion where a washing sink 4 for placing an endoscope 50 to be washed/disinfected and a tube washing brush unit setting portion 5 are exposed.

The washing sink 4 includes an operation portion placing vessel 6 that matches the shape of a grasping portion 51 configuring an operation portion of the endoscope 50, and an insertion portion placing vessel 7 for circularly placing an insertion portion 52 of the endoscope 50.

The insertion portion placing vessel 7 is provided with: a plurality of holding members 4a for separately holding circular portions of the insertion portion 52 with a predetermined interval therebetween; and a washing case setting portion 4b located at a center portion of the vessel, for setting a washing case, not shown, in which buttons, forceps stoppers, and the like of the endoscope 50 are placed to be washed and disinfected together with the endoscope 50.

The operation portion placing vessel 6 is provided, at predetermined positions thereof, with a fluid supplying unit 26 having a leak detection nozzle 25 (see FIG. 3) and a plurality of supply nozzles for supplying fluid to individual tubes. The nozzles of the fluid supplying unit 26 are inserted into a base mounting portion 23 provided at the grasping portion 51. For example, the leak detection nozzle 25 (see FIG. 3) for supplying air to an inner space 61 of the endoscope 50 is inserted into an inner space base 24 (see FIG. 3) which communicates with the inner space 61 (see FIG. 6A).

The fluid supplying unit 26 is provided with an automatic mounting/dismounting portion 103 (see FIG. 5) for advancing to and withdrawing from the base mounting portion 23. The automatic mounting/dismounting portion 103 is driven and controlled by a control unit 102 (see FIG. 5), so that the various nozzles including the leak detection nozzle 25 are automatically mounted on the base mounting portion 23 of the grasping portion 51.

The tube washing brush unit setting portion 5 arranged near the operation portion placing vessel 6 is provided with a supply nozzle mounting/dismounting mechanism portion for permitting the supply nozzles to advance to and withdraw from the grasping portion 51, so that the supply nozzles can be coupled to or decoupled from tube bases of treatment tool inserting tubes which also serve as suction tubes. A tube washing brush unit 20 is detachably provided at the tube washing brush unit setting portion 5.

The top cover 3 of the washing apparatus 1 is formed with a cassette cover portion 3a having a recessed shape as viewed from backside. The cassette cover portion 3a plays a roll in preventing contact between the top cover 3 and the tube washing brush unit 20 set at the tube washing brush unit setting portion 5, when the top cover 3 is closed. Since the top cover 3 is formed of a transparent or semi-transparent member, the interior of the washing sink 4 and the tube washing brush unit 20 can be observed in the state where the top cover 3 is closed.

As shown in FIG. 2, the top cover 3 has a top face provided with an operation instructing portion 8 for performing various setting operations, such as threshold setting for leak detection processes and various conditions setting for washing and disinfecting processes.

The operation instructing portion 8 is provided with a displaying portion 106 for indicating, for example: process conditions, such as start, stop or a leak detection process; elapsed time; or warning in the leak detection processes.

The apparatus body 2 of the endoscope washing and disinfecting apparatus 1 incorporates a piping network interposed with a solenoid valve, a check valve and the like, a washing and disinfecting pump, a leak detection pump and a compressor, in order to circulate washing solution, disinfectant solution, rinse, alcohol and air to the washing sink 4 and the tube washing brush unit setting portion 5 in performing various processes (washing, disinfecting, alcohol flushing and dehydrating processes).

The apparatus body 2 also incorporates the control unit 102 (see FIG. 5) for driving and stopping various electrical devices according to programming of the various processes mentioned above.

Various tanks (not shown) are arranged in the apparatus body 2, which contain fluids of washing solution, disinfectant solution and alcohol. Also, a hose or the like, not shown, is connected to the apparatus body 2 of the washing apparatus 1 to supply tap water from a water faucet, for rinsing or for diluting washing and disinfectant solutions. In performing leak detection as well, tap water is stored in the washing sink 4, so that leak detection of the endoscope 50 can be carried out in a state where the endoscope 50 is immersed in the water stored in the washing sink 4.

An explanation hereinafter will be given on the endoscope 50 for which leak detection, for example, is carried out by the washing apparatus 1 according to the present embodiment. The grasping portion 51 of the endoscope 50 is not provided with a driving portion or a bending operation portion for manually or electrically bending a bending portion 54. As a matter of course, the endoscope may be a conventional endoscope which enables manual or electrical bending operation through an external device, for example.

As shown in FIG. 3, the endoscope 50 has: a distal end portion 53 which is provided, for example, with an image pickup portion for picking up images of an image-pickup target, an illuminating portion and a forceps opening; the grasping portion 51; the elongated insertion portion 52 extended on the side of the distal end portion 53 of the grasping portion 51; and the bending portion 54 arranged on the side of the distal end portion 53 of the insertion portion 52 to bend the distal end portion 53.

When in use, the driving portion, which is an external device, is mechanically connected to a bending transmitting portion 55 which is arranged at the grasping portion 51 of the endoscope 50 to provide the bending portion 54 with bending motion using the driving force from the driving portion. A controller is connected to the driving portion so that the user can operate the controller to control the operation of the driving portion, thereby performing desired bending operation can be performed.

Referring now to FIG. 4, hereinafter is explained a specific configuration of each of the bending transmitting portion 55, a connecting portion 30 and a distal end driving portion 21, configuring a principal part of the washing apparatus 1.

As shown in FIG. 4, the operation portion placing vessel 6 of the washing sink 4 is provided with the connecting portion 30 which is connected to the bending transmitting portion 55 of the endoscope 50 to transmit driving force to the bending transmitting portion 55. The connecting portion 30 is provided with a transmission member 32 of the distal end driving portion 21, which will be described later, so as to be projected therefrom.

The bending transmitting portion 55 provided in the grasping portion 51 of the endoscope 50 has a group of gears, for example, not shown, for appropriately pulling and releasing a plurality of bending operation wires 56. When coupled to the transmission member 32 of the distal end driving portion 21, the bending transmitting portion 55 can use the driving force from the transmission member 32 for bending operation of the bending portion 54 in different directions through the wires 56.

The transmission member 32 is rotatably and water-tightly inserted through the operation portion placing vessel 6 in the vicinity of substantially the center of the connecting portion 30. The transmission member 32 has an end portion to which a gear 33 is fixed, the gear being provided within and near the operation portion placing vessel 6. The transmission member 32 is axially supported by the connecting portion 30 of the operation portion placing vessel 6 and a bearing 31 so as to achieve smooth rotational movement.

As mentioned above, an insertion portion of the transmission member 32 is configured to obtain water-tightness. Meanwhile, the distal end driving portion 21 is arranged on the other side of the operation portion placing vessel 6, i.e. the side opposite to the connecting portion 30, to transmit driving force through the transmission member 32 and to generate the driving force.

The distal end driving portion 21 has the transmission member 32, the gear 33 provided at a proximal end portion of the transmission member 32, a gear 34 engaging with the gear 33 and a motor 35 having a drive shaft for rotating the gear 34 and serving as a drive source.

In the washing apparatus 1 having the configuration described above, when leak detection processes and washing and disinfecting processes are performed, the endoscope 50 is placed in the washing sink 4, and at the same time, the grasping portion 51 is placed in the operation portion placing vessel 6. In this case, the grasping portion 51 is mounted by inserting the projected transmission member 32 through a connecting portion 51a provided at the grasping portion 51 and connecting the connecting portion 51a with the connecting portion 30. Thus, the transmission member 32 of the distal end driving portion 21 is coupled to the bending transmitting portion 55 of the grasping portion 51.

The distal end driving portion 21 is driven and controlled by the control unit 102 that will be described later.

Referring now to FIG. 5, hereinafter is described the configuration of the apparatus body 2 of the washing apparatus 1 according to the present embodiment.

As shown in FIG. 5, the apparatus body 2 of the washing apparatus 1 has a main part including a flow supplying portion 100, a mounting/dismounting detecting portion 101, the control unit 102 that controls the entire washing apparatus 1, the automatic mounting/dismounting portion 103 which can automatically mount/dismount the fluid supplying unit 26 provided at the operation portion placing vessel 6 and the tube washing brush unit setting portion 5 on/from various bases of the endoscope 50, a distal end driving portion 104, a pressure detecting portion 105, a results notifying portion 106 and an operation instructing portion 8.

The flow supplying portion 100 is configured by, for example, a washing and disinfecting pump for supplying disinfectant solution or washing solution to a forward water supply nozzle, a water supply nozzle and an air supply nozzle of the fluid supplying unit 26, and a leak detection pump for supplying gas, such as air, to the leak detection nozzle of the fluid supplying unit 26. The flow supplying portion 100 also has a member for storing tap water in the washing sink 4 when the leak detection operation is performed.

The mounting/dismounting detecting portion 101 detects mounting/dismounting of the various nozzles of the fluid supplying unit 26 when such nozzles have been mounted on the base mounting portion 23 of the endoscope 50, and outputs the results of the detection to the control unit 102. The mounting/dismounting detecting portion 101 also detects mounting/dismounting of the connecting portion 30 of the operation portion placing vessel 6 on/from the connecting portion 51a of the grasping portion 51 of the endoscope 50, and outputs the results of the detection to the control unit 102.

It should be appreciated that the detection performed by the mounting/dismounting detecting portion 101 may be based on any principle, not particularly being limited.

The automatic mounting/dismounting portion 103 has, for example, a driving mechanism portion and a nozzle mounting/dismounting mechanism portion, so that the fluid supplying unit 26 provided at the operation portion placing vessel 6 and the tube washing brush unit setting portion 5 can be automatically mounted/dismounted on/from the various bases of the endoscope 50.

The distal end driving portion 104 is the same as the distal end driving portion 21 explained referring to FIG. 4.

The pressure detecting portion 105 has a pressure sensor, for example, to detect pressure in the inner space 61 of the endoscope 50 when the leak detection processes are performed and outputs the results of the detection to the control unit 102.

The results notifying portion 106 is provided in the operation instructing portion 8 (see FIG. 2), for example, and plays a roll in visually or audibly notifying the results of leak detection.

The control unit 102 controls the entire washing apparatus 1, that is, controls the flow supplying portion 100, the automatic mounting/dismounting portion 103, the distal end driving portion 104, the results notifying portion 106, and the like.

In performing leak detection of the endoscope 50, the control unit 102 drives the distal end driving portion 104 to control the bending portion 54 of the endoscope 50 so as to be bent in different directions. Meanwhile, the control unit 102 compares the pressure in the inner space 61 detected by the pressure detecting portion 105 with a preset threshold, and determines occurrence or nonoccurrence of water leak of the endoscope 50 based on the results of the comparison.

Specifically, as shown in FIG. 6A, if the bending portion 54 has been extremely bent, for example, a hole formed in the bending portion 54 and being in communication with the outside may be closed up, depending on the direction of the bending. In this case, in spite of the fact that water leak has occurred, a determination may be made that water leak has not occurred. Thus, there is possibility that leak detection may not be correctly performed. In this regard, as shown in FIGS. 6A and 6B, the washing apparatus 1 can perform leak detection, while the bending portion 54 is being bent in different directions (direction "A" or "B").

If the pressure in the inner space 61 detected by the pressure detecting portion 105 is larger than the preset threshold, the control unit 102 produces a signal indicating that no water leak has been found in the endoscope 50, based on the comparison result, and outputs the signal to the results notifying portion 106. On the other hand, if the pressure detected by the pressure detecting portion 105 is equal to or smaller than the preset threshold, the control unit 102 produces a warning signal indicating that water leak has been found in the endoscope 50, based on the comparison result, and outputs the signal to the results notifying portion 106.

It should be appreciated that the threshold is stored in a storing portion, not shown, and that the control unit 102 reads out the threshold for comparison when the leak detection is performed. The threshold is changeable by the operation instructing portion 8.

Referring to FIGS. 7 and 8, hereinafter is described a procedure for the leak detection method performed by the washing apparatus 1. The description hereinafter is provided assuming that the user is to carry out leak detection processes and washing and disinfecting processes of the endoscope 50, using the washing apparatus 1 shown in FIG. 1. The washing apparatus 1 is capable of implementing both an automatic leak detection mode for automatically performing the leak detection processes and a manual leak detection mode for manually performing the leak detection processes.

First, referring to FIG. 7, an explanation is provided on the procedure in the case where the washing apparatus 1 performs processes in the automatic leak detection mode.

At step S1, the endoscope 50 is set by the user at the washing sink 4 of the apparatus body 2. In this case, the user inserts the transmission member 32 projected upward from the operation portion placing vessel 6, into the connecting portion 51a of the endoscope 50, so that the connecting portion 51a is connected to the connecting portion 30. Thus, the transmission member 32 of the distal end driving portion 21 is coupled to the bending transmitting portion 55.

At step S2, with the user's operation of selecting the automatic leak detection mode through the operation instructing portion 8, the control unit 102 reads out a program of the procedure, shown in FIG. 7, from the storing portion, not shown, to start the automatic leak detection processes.

At step S3, the control unit 102 controls the automatic mounting/dismounting portion 103 to control a connecting step where the fluid supplying unit 26 provided at the operation portion placing vessel 6 and the tube washing brush unit setting portion 5 are automatically mounted on the base mounting portion 23 that includes the inner space base 24 of the endoscope 50.

At step S4, the control unit 102 controls a pressurizing step, by which the leak detection pump (not shown) of the flow supplying portion 100 supplies air to the inner space 61 of the endoscope 50.

For example, the control unit 102 controls the leak detection pump so that the pressure in the inner space 61 of the endoscope 50 will be increased up to 0.03 MPa. In particular, at step S5, the control unit 102 makes a comparison referring to the detection results derived from the pressure detecting portion 105, and stops the leak detection pump to stop pressurization when the pressure in the inner space 61 of the endoscope 50 has reached 0.03 MPa. Then, tap water is supplied to the washing sink 4 to bring the endoscope 50, or more precisely, the distal end portion 53, the bending portion 54 and the insertion portion 52 of the endoscope 50, into a state of being immersed in the water stored in the washing sink 4. In the automatic leak detection mode, there may be a case where the endoscope 50 need not be immersed in water. However, the endoscope 50 may, here, be immersed in water, in case of revealing possible formation of a hole in the automatic leak detection mode, in which case the manual leak detection may resultantly be performed.

Subsequently, at step S6, the control unit 102 controls a bending portion driving step, by which the distal end driving portion 21 is driven. Then, the motor 35 of the distal end driving portion 21 is rotated to rotate the transmission member 32 through the gears 34 and 33. Thus, the driving force is transmitted to the bending transmitting portion 55 in the grasping portion 51, which is coupled to the transmission member 32, whereby the bending portion 54 of the insertion portion 52 is bent in the vertical and horizontal directions. The bending motion may be sequentially imparted in the vertical and horizontal directions, or may be imparted in combined directions of vertical and horizontal directions, such as an upper right direction or a lower left direction.

Then, at step S7, the control unit 102 controls a detecting step at which the pressure detecting portion 105 measures the pressure in the inner space 61 of the endoscope 50. Then, the control unit 102 controls a determining step at which a comparison is made between the results of the measurement and the preset threshold read out from the storing portion, not shown. The threshold here is preset to 0.02 MPa, for example.

If the measurement result exceeds 0.02 MPa, it is determined that no water leak has occurred, and control proceeds to step S8. If the measurement result is equal to or less than 0.02 MPa, the control unit 102 determines that water leak has occurred, and control proceeds to step S10.

At step S8, the control unit 102 produces a signal indicative of "No leak occurred", for example, and causes the results notifying portion 106 to provide a visual indication or audible reproduction. Then, at step S9, the control unit 102 ends the leak detection processes and at the same time starts the washing and disinfecting processes for the endoscope 50.

On the other hand, at step S10, the control unit 102 effects control so that the leak detection pump is turned off or the fluid supplying unit is separated from the endoscope 50, thereby stopping the leak detection processes.

After that, at step S11, the control unit 102 outputs a signal indicative of the occurrence of leak to the results notifying portion 106. In response, the results notifying portion 106 provides a visual indication or audible reproduction of the information, for example, "Holes may be present in endoscope. Please carry out manual leak detection". Note that giving the notification of carrying out the manual leak detection has a purpose having a user carry out another leak detection for reconfirmation.

As shown in FIG. 6A, with the conventional automatic leak detection method, even when there is a hole 60 in a portion of the bending portion 54, communicating with the inner space 61, water leak may be determined as not being found, if the bending portion 54 is bent in the direction "B" where the hole 60 is involved on a large scale and the hole 60 is closed up by a rubber-covered portion covering the bending portion 54.

In this regard, the leak detection method performed by the washing apparatus 1 according to the present embodiment, can perform leak detection while the distal end driving portion 21 is being driven to bend the bending portion 54 in different directions. Thus, if the hole 60 is present, the bending portion 54 is also automatically bent on a grand scale in the direction "A", as shown in FIG. 6B, where there is no involvement of the hole 60. Accordingly, gas is blown out into the water in the washing sink 4, and thus the pressure in the inner space 61 is reduced.

In this way, the leak detection method described above can automatically perform leak detection for the insertion portion 52, while the bending portion 54 of the endoscope 50 is driven in different directions.

Referring now to FIG. 8, hereinafter is described a procedure for the manual leak detection mode of the leak detection method according to the present embodiment.

At step S19, the endoscope 50 is placed, by the user, in the washing sink 4 of the apparatus body 2. In this case, the user inserts the transmission member 32 projected upward from the operation portion placing vessel 6 into the connecting portion 51a of the grasping portion 51 provided at the endoscope 50, so that the connecting portion 51a is connected to the connecting portion 30 and mounted thereon. Thus, the transmission member 32 of the distal end driving portion 21 is coupled to the bending transmitting portion 55 of the grasping portion 51.

At step S20, upon user's selection of the manual leak detection mode through the operation instructing portion 8, the control unit 102 reads out a program of the procedure shown in FIG. 8 from the storing portion, not shown, to start the manual leak detection processes.

At step S21, the control unit 102 controls the automatic mounting/dismounting portion 103 to automatically mount the fluid supplying unit 26 provided at the operation portion placing vessel 6 and the tube washing brush unit setting portion 5, onto respective bases of the endoscope 50.

Then, at step S22, the control unit 102 permits the leak detection pump of the flow supplying portion 100 to supply air into the inner space 61 of the endoscope 50. In this case, the control unit 102 effects control so that the air in the inner space 61 of the endoscope 50 is pressurized up to 0.03 MPa, for example.

Then, the control unit 102 makes a comparison referring to the detection results derived from the pressure detecting portion 105, and stops the leak detection pump when the pressure in the inner space 61 of the endoscope 50 has reached 0.03 MPa. Subsequently, at step S23, the control unit 102 permits a valve to open, so that tap water is stored in the washing sink 4 up to a level sufficient for immersing the endoscope 50, or more precisely, the distal end portion 53, the bending portion 54 and the insertion portion 52 of the endoscope 50. The user may store tap water in the washing sink 4 in a manual manner. After a predetermined amount of tap water has been stored in the washing sink 4, the control unit 102 sounds a buzzer or provides a visual indication, at step S24, through the results notifying portion 106 of the operation instructing portion 8 to notify that leak detection is available.

Upon reception of the user's operation of pressing a check start SW at step S25, the control unit 102 drives the distal end driving portion 104 (21), at step S26. Then, the motor 35 of the distal end driving portion 104 (21) is rotated to rotate the transmission member 32 through the gears 34 and 33. Thus, the driving force is transmitted to the bending transmitting portion 55 in the grasping portion 51, which is coupled to the transmission member 32, with a result that the bending portion 54 of the insertion portion 52 is bent in different directions (vertical and horizontal directions).

In the manual leak detection method, at step S27, the user himself or herself can take a look at the insertion portion 52 which is immersed in the water of the washing sink 4 and whose distal end portion 53 is moved in different directions with the bending motion of the bending portion 54, and can determine the occurrence or nonoccurrence of water leak.

In this case, the user is able to visually check the presence of the hole 60 in the insertion portion 52, or the occurrence or nonoccurrence, by taking a look at the insertion portion 52 which is in motion as shown in FIGS. 6A and 6B, as described above, and by confirming bubbles coming out of the hole 60.

If it is determined that no water leak has occurred, the user can then end the leak detection, at step S28, and at the same time, can operate the operation instructing portion 8 to perform the washing and disinfecting processes.

Then, at step S29, the control unit 102 drives the flow supplying portion 100 and the like so that the washing and disinfecting processes can be performed.

On the other hand, if the user determines, at step S27, that water leak has occurred, control proceeds to step S30 where the user can operate the operation instructing portion 8 to end the leak detection processes.

Then, at step S31, the control unit 102 permits a valve to open to drain the tap water in the washing sink 4, and ends the leak detection processes.

In this case, since there is water leak in the insertion portion of the endoscope 50, the control unit 102 permits the results notifying portion 106 to give visual or audible notification of, for example, "Water leak has been detected in the endoscope. Please repair.", and then ends the processes.

As described above, when leak detection operation is performed, the leak detection method performed by the washing apparatus 1 according to the present embodiment makes it possible to automatically perform leak detection of the insertion portion 52, with the bending portion 54 being driven in different directions. Also, when the manual leak detection method is performed as well, leak detection of the insertion portion of the endoscope 50 can be performed in a manner similar to the automatic leak detection method.

Figure 9:
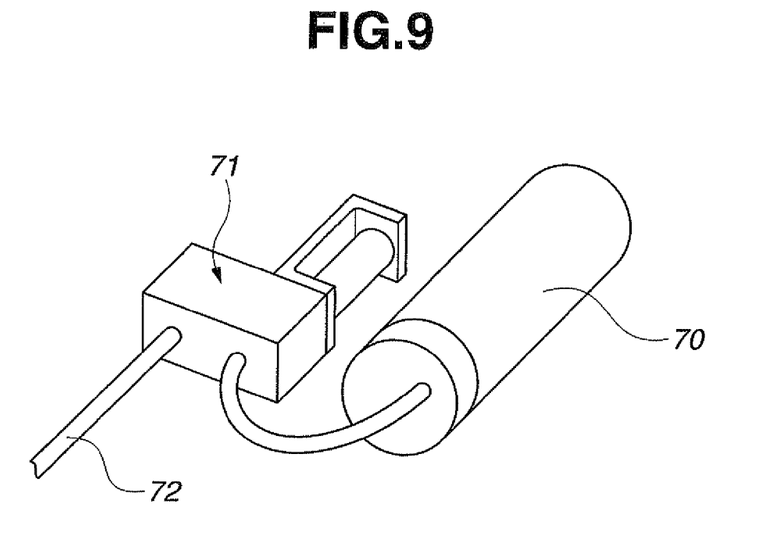
FIG. 9 is a schematic diagram illustrating a configuration of a flow supplying portion having a leak detection pump.
Figure 10:
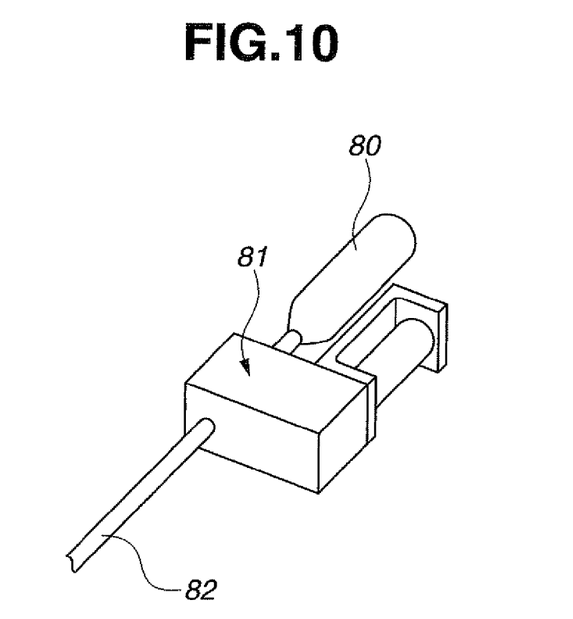
FIG. 10 is a schematic diagram illustrating a configuration of a flow supplying portion having an air cylinder.
Figure 11:
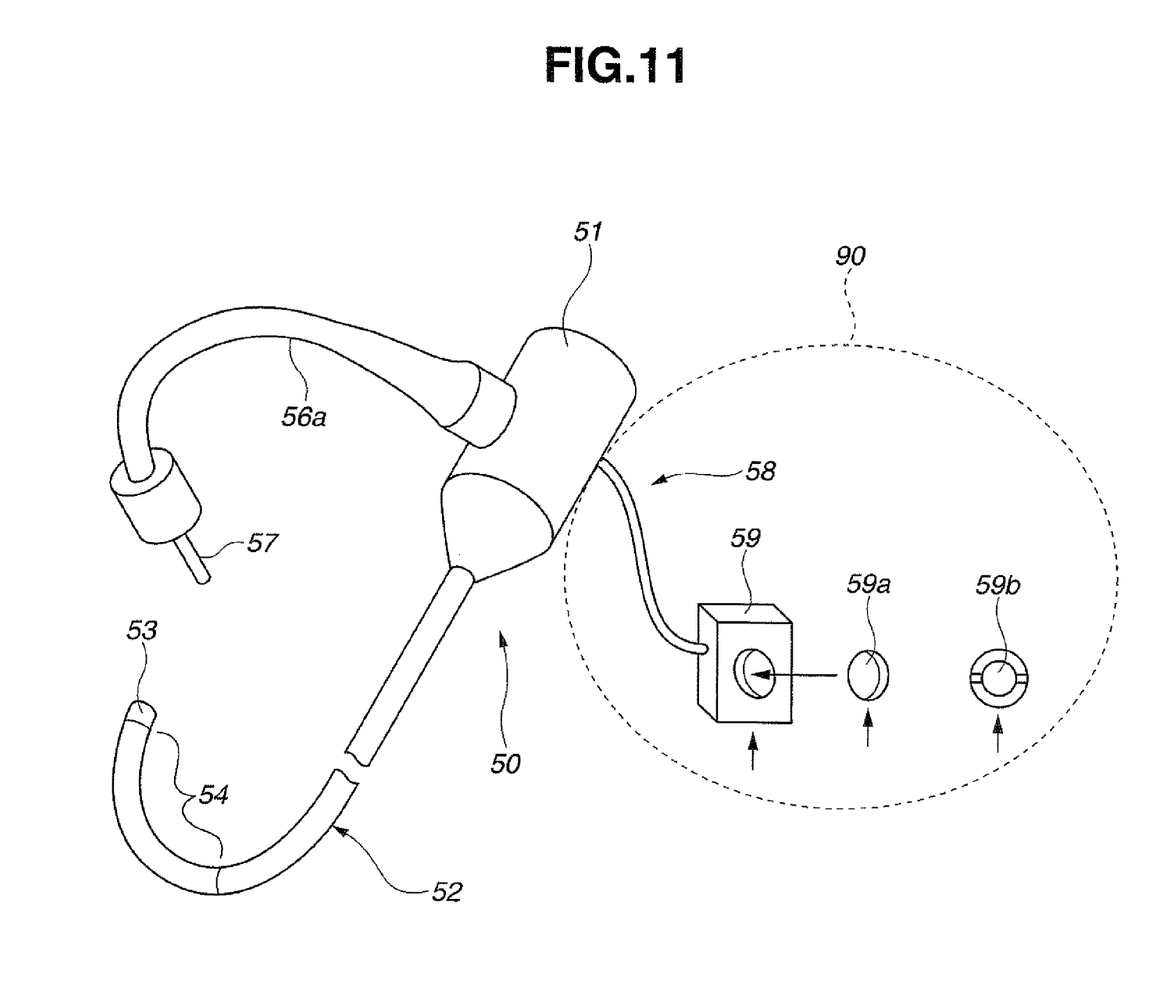
FIG. 11 is a schematic diagram illustrating a configuration of an endoscope and a controller to be connected to the endoscope in the endoscope washing apparatus, according to the embodiment.

The washing apparatus 1 according to the present embodiment may use the technique as disclosed in FIGS. 9 to 11. FIG. 9 is a schematic diagram illustrating a configuration of a flow supplying portion having a leak detection pump. FIG. 10 is a schematic diagram illustrating a configuration of a flow supplying portion having an air cylinder.

As shown in FIG. 9, in the washing apparatus 1, a flow supplying portion 71 permits a leak detection pump 70 having a motor (not shown) to supply air for performing leak detection to a leak detection tube 72. However, since such a motor has a short life, the endurance time of the leak detection pump 70 has tended to be short or failure has tended to be caused. Further, since the configuration per se of the leak detection pump 70 is large, the apparatus body 2 has often resulted in a large size.

To take measures against the issues mentioned above, as shown in FIG. 10, a flow supplying portion 81 may be provided with a detachable cartridge type air cylinder 80 which is filled with compressed air. Thus, the flow supplying portion 81 can supply the compressed air in the air cylinder 80.

The washing apparatus 1 can be configured to use and mount the cartridge type air cylinder 80 on the flow supplying portion 81, thereby preventing failure of the motor. In addition, by changing the air cylinder 80, the operating time can be prevented from being limited. Also, the air cylinder 80, whose size is smaller than the leak detection pump 70, can contribute to reducing the size of the apparatus body 2.

FIG. 11 is a schematic diagram illustrating the configuration of an endoscope and a controller to be connected to the endoscope in the endoscope washing apparatus according to the embodiment.

A bending operation portion, when it is provided at a grasping portion in a conventional endoscope, has been given an uneven shape. Accordingly, some measure for locally supplying water flow, for example, has been required to be taken when the endoscope is washed/disinfected. Because of this, the washing apparatus have suffered from disadvantages of unavoidably having a complicated configuration, or of creating additional labor of washing and disinfecting an uneven shape portion, such as the bending operation portion, in manually conducting washing/disinfection.

To take measures against the issues mentioned above, as shown in FIG. 11, the washing apparatus 1 according to the present embodiment is configured to locate the endoscope 50 in the washing sink 4, with the bending operation portion being eliminated from the grasping portion 51, so that the workability of the washing and disinfecting processes can be enhanced.

In other words, the grasping portion 51 of the endoscope 50 is not provided with the bending operation portion for manually or electrically bending the bending portion 54. Also, during endoscopy or endoscopic treatment, connection can be established with a driving portion, which is an external device, through a universal cord 56a. Thus, the driving force from the driving portion is transmitted to the bending transmitting portion 55 in the grasping portion 51 to enable bending motion. In this case, a connector 57 having a proximal end portion of the universal cord 56a is coupled to the driving portion, not shown, to establish the connection.

Further, the grasping portion 51 shown in FIG. 11 is detachably and electrically connected with a disposable control portion 90. The disposable control portion 90 has a connecting cable 58 and a controller 59 electrically connected to the connecting cable 58.

The controller 59 is configured, for example, by rotatably fixing a trackball 59a thereto using a receiving member 59b. In particular, in carrying out bending operation of the bending portion 54 of the endoscope 50, the user can properly rotate the trackball 59a of the controller 59 and perform the bending operation of the bending portion 54 in a desired direction.

The controller 59 may be configured by providing a different instructing portion for bending operation direction, without being limited to the trackball 59a.

Thus, with the configuration described above, the disposable control portion 90 can be removed from the endoscope 50 and disposed after completing endoscopy or endoscopic treatment, and then only the endoscope 50 can be located in the washing sink 4 to be given the leak detection processes and the washing and disinfecting processes. At the same time, the washing and disinfecting processes can be performed for the grasping portion 51 having no uneven shape, owing to the removal of the bending operation portion. Thus, not only washing and disinfecting effect but also washing and disinfecting workability can be enhanced.

Having described the embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope washing and disinfecting apparatus comprising:
    a connecting portion for transmitting driving force, the connecting portion being connected to a bending transmitting portion of an endoscope comprising a distal end portion, a bending portion, an insertion portion, a grasping portion, and the bending transmitting portion provided at the grasping portion to provide the bending portion with bending motion, wherein the connecting portion comprises, at least one gear and a motor, the motor controlled by a control unit and wherein the bending transmitting portion comprises one or more gears operatively connected to a plurality of wires, the plurality of wires configured to produce the bending motion of the bending portion;

a distal end driving portion for transmitting driving force to the bending transmitting portion through the connecting portion;

a fluid supplying unit for supplying gas into an inner space of the endoscope;

a pressure detecting portion for detecting pressure in the inner space; and the control unit for controlling the distal end driving portion to provide the bending portion with bending motion, and for determining occurrence or nonoccurrence of water leak of the endoscope by comparing the pressure detected by the pressure detecting portion with a preset threshold.

2. The endoscope washing and disinfecting apparatus according to claim 1, wherein:

the apparatus further comprises a washing and disinfecting sink for storing water; and the control unit determines occurrence or nonoccurrence of the water leak in a state where the endoscope is immersed in the water stored in the washing sink.

3. The endoscope washing and disinfecting apparatus according to claim 2, wherein:

the apparatus further comprises a results notifying portion for notifying a determination result from the control unit as to occurrence or nonoccurrence of the water leak in at least either a visual or audible manner; and the control unit outputs a signal to the results notifying portion indicating that water leak has not occurred in the endoscope, if the pressure detected by the pressure detecting portion exceeds the threshold, and outputs a signal to the results notifying portion indicating that water leak has occurred in the endoscope, if the pressure detected by the pressure detecting portion is equal to or less than the threshold.

4. The endoscope washing and disinfecting apparatus according to claim 1, wherein:

the fluid supplying unit supplies the gas from an air cylinder.

5. A leak detection method performed by an endoscope washing and disinfecting apparatus comprising:

a connecting step for connecting a connection portion to an inner space base of an endoscope comprising a distal end portion, a bending portion, an insertion portion, a grasping portion, a bending transmitting portion provided at the grasping portion to provide the bending portion with bending motion, wherein the bending transmitting portion comprises one or more gears operatively connected to a plurality of wires, the plurality of wires configured to produce the bending motion of the bending portion, and the inner space base provided at the grasping portion and communicating with an inner space of the insertion portion, to a fluid supplying unit of the endoscope washing and disinfecting apparatus comprising a distal end driving portion for transmitting driving force to the bending transmitting portion through a connecting portion, the fluid supplying unit, and a pressure detecting portion, wherein the connecting portion comprises, at least one gear and a motor, the motor controlled by a control unit;

a pressurizing step for supplying gas to the inner space from the fluid supplying unit;

a bending portion driving step for bending the bending portion by driving the distal end driving portion;

a detecting step for detecting pressure in the inner space by the pressure detecting portion; and a determining step for determining occurrence or nonoccurrence of water leak in the endoscope by comparing the pressure in the inner space and a preset threshold.

6. The leak detection method performed by the endoscope washing and disinfecting apparatus according to claim 5, wherein:

the endoscope washing and disinfecting apparatus further comprises a washing and disinfecting sink for storing water; and the determining step is performed in a state where the endoscope is immersed in the water stored in the washing sink.

7. The leak detection method performed by the endoscope washing and disinfecting apparatus according to claim 5, wherein:

the endoscope washing and disinfecting apparatus further comprises a results notifying portion for notifying a determination result as to occurrence or nonoccurrence of the water leak in at least either a visual or audible manner; and the determining step determines water leak as not having occurred if the pressure detected in the detecting step exceeds a preset threshold, and determines water leak as having occurred if the pressure detected in the detecting step is equal to or less than the preset threshold.

* * * * *